US008664005B2

(12) United States Patent
Nishigaki et al.

(10) Patent No.: US 8,664,005 B2
(45) Date of Patent: Mar. 4, 2014

(54) METHOD FOR INTRODUCING AND TRANSFERRING MULTIPLE MINUTE QUANTITY SAMPLES

(75) Inventors: Koichi Nishigaki, Saitama (JP); Takahiro Tayama, Saitama (JP); Yasunorl Kinoshita, Saitama (JP); Hidekazu Uchida, Saitama (JP)

(73) Assignee: National University Corporation Saitama University, Saitama (JP)

( * ) Notice: Subject to any disclaimer, the term of this patent is extended or adjusted under 35 U.S.C. 154(b) by 1404 days.

(21) Appl. No.: 11/884,672

(22) PCT Filed: Feb. 17, 2006

(86) PCT No.: PCT/JP2006/302888
§ 371 (c)(1),
(2), (4) Date: May 28, 2008

(87) PCT Pub. No.: WO2006/088162
PCT Pub. Date: Aug. 24, 2006

(65) Prior Publication Data
US 2008/0272066 A1 Nov. 6, 2008

(30) Foreign Application Priority Data
Feb. 18, 2005 (JP) .................................. 2005-042885

(51) Int. Cl.
*G01N 15/06* (2006.01)
(52) U.S. Cl.
USPC ............ 436/180; 422/68.1; 422/100; 436/43; 436/174; 436/178
(58) Field of Classification Search
USPC ............ 422/68.1, 100; 436/43, 174, 178, 180
See application file for complete search history.

(56) References Cited

U.S. PATENT DOCUMENTS

| 3,378,481 | A | * | 4/1968 | Saravis et al. ................. 204/641 |
| 4,912,057 | A | * | 3/1990 | Guirguis et al. ........... 435/288.4 |
| 5,039,493 | A | * | 8/1991 | Oprandy ....................... 422/534 |
| 6,193,642 | B1 | | 2/2001 | Hristake ......................... 494/20 |
| 6,627,447 | B2 | | 9/2003 | Burbaum et al. ............... 436/45 |
| 6,838,051 | B2 | * | 1/2005 | Marquiss et al. ............... 422/63 |
| 6,849,462 | B1 | * | 2/2005 | Winkler et al. ................. 506/16 |
| 2005/0266582 | A1 | * | 12/2005 | Modlin et al. ................. 436/164 |

FOREIGN PATENT DOCUMENTS

| CN | 1244140 A | 9/2000 |
| EP | 0989912 | 8/2005 |
| JP | 2001-509272 A | 7/2001 |

(Continued)

*Primary Examiner* — Brian J Sines
(74) *Attorney, Agent, or Firm* — Jacobson Holman PLLC

(57) ABSTRACT

A method of introducing solution into the wells of a multiwell plate comprised of a substrate having multiple wells on at least one principal surface thereof. The wells are imparted dimensions, shapes, and surface configurations such that when said multiwell plate is positioned in stationary fashion with the openings of said wells facing upward, said solution does not enter said wells even when the openings of said wells are covered by said solution, and the solution is positioned on said principal surface of said multiwell plate having wells and a centrifugal force oriented from the well opening toward the bottom is applied to introduce said solution into said wells. Provided is a method for conveniently filling vessels (wells) with a solution such as a reaction solution, even when the vessels (wells) number in excess of 1,000, and even when the dimension, shape, and surface configuration of the vessels (wells) do not permit fluid to flow into the vessels (wells).

12 Claims, 9 Drawing Sheets

(56) References Cited

FOREIGN PATENT DOCUMENTS

| | | |
|---|---|---|
| JP | 2001-517789 A | 10/2001 |
| JP | 2002-502955 A | 1/2002 |
| JP | 2005-118985 A | 5/2005 |
| WO | 9831466 | 7/1998 |
| WO | 9951349 | 10/1999 |
| WO | 0066267 | 11/2000 |
| WO | 0133211 | 5/2001 |
| WO | WO 02/41996 A1 | 5/2002 |
| WO | 03028878 | 4/2003 |
| WO | WO 03/041863 A2 | 5/2003 |
| WO | WO 03/102578 A2 | 12/2003 |

* cited by examiner

Fig. 5
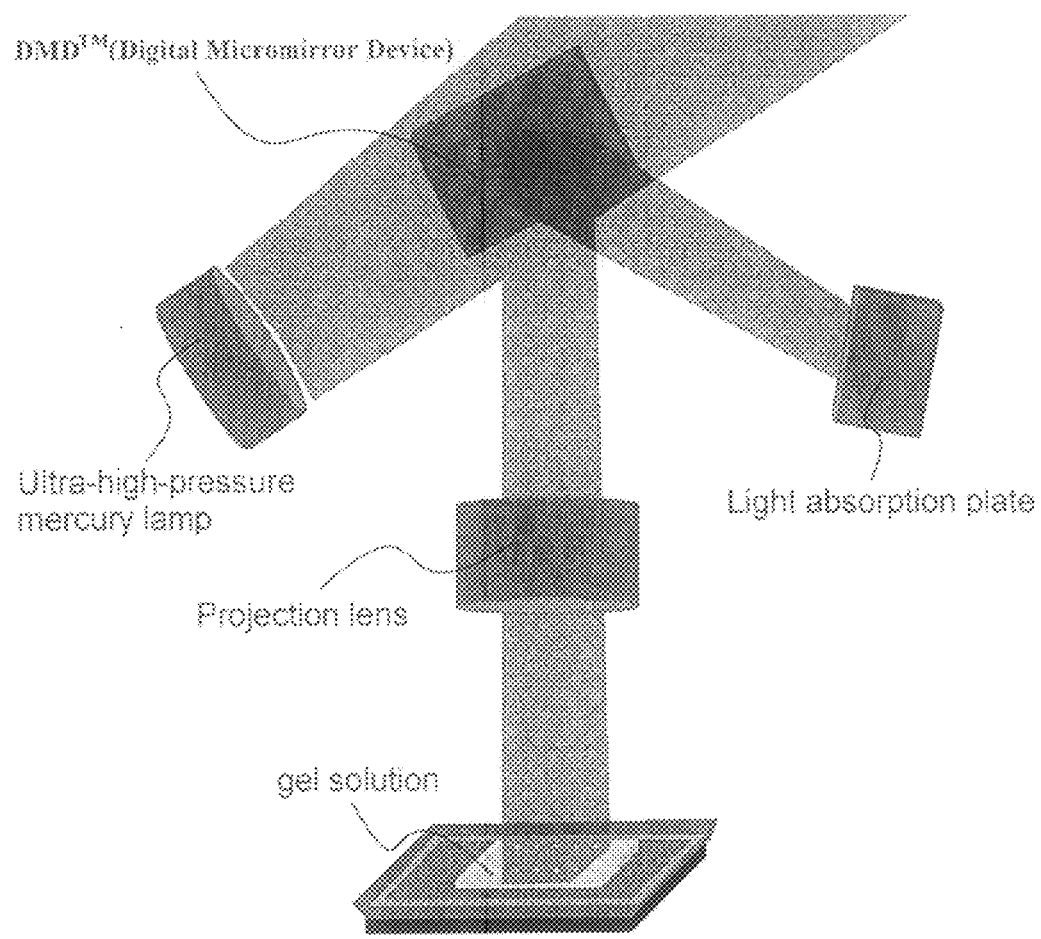
Fig. 6
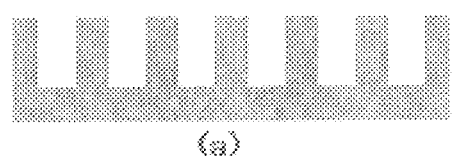 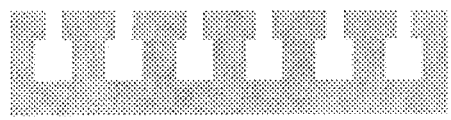
(a) Standard MMV    (b) MMV with wells having narrowed upper parts (a) Standard MMV   (b) MMV with wells having narrowed upper parts Fig. 10
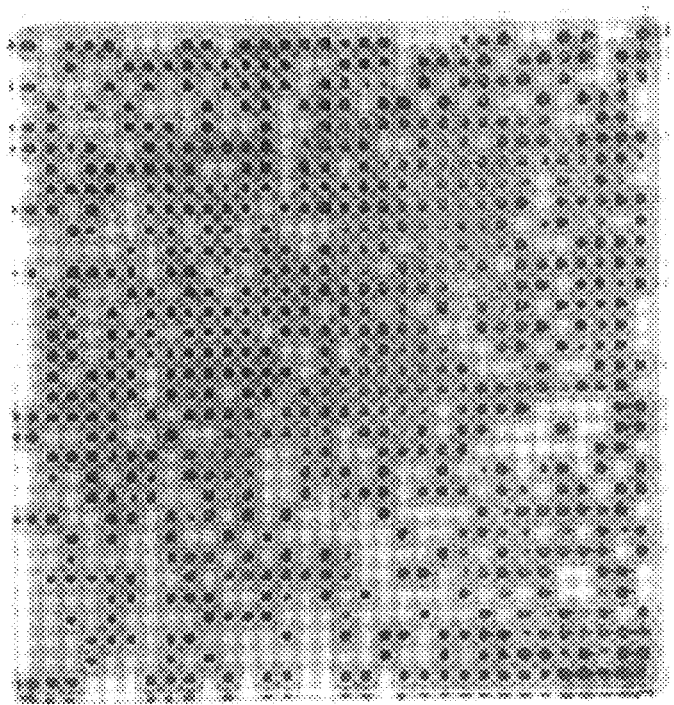
Image
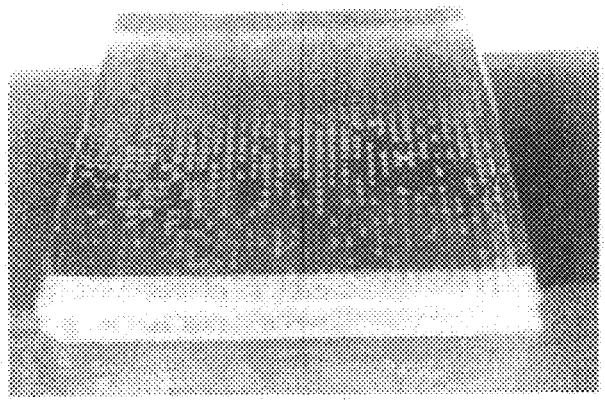
Photo graph

US 8,664,005 B2

METHOD FOR INTRODUCING AND TRANSFERRING MULTIPLE MINUTE QUANTITY SAMPLES

This is a of PCT/JP2006/302888 filed Feb. 17, 2006.

TECHNICAL FIELD

The present invention relates to a method for simultaneously introducing and transferring multiple minute quantity liquid samples to a vessel in parallel fashion. More particularly, the present invention relates to a method permitting the simultaneous separation of samples in parallel fashion required when reacting multiple minute liquid samples in evolutionary engineering, pharmaceuticals, food, bioventures, clinical examination agencies, agencies for checking the toxicity of compound substances, and the like.

BACKGROUND ART

The coating or binding of multiple (for example, 1,000 or more) minute (for example, sub-nanoliter) samples on a plate and the simultaneous identical processing thereof has been developed in the form of microplates. An on-beads method of binding individual samples onto separate beads has also been developed.

However, a special device (microplotter or microdispenser) is required to coat the sample on the plate in these conventional methods, and they require time and effort. Further, only certain reaction conditions are normally possible for reacting samples that have been coated in this manner. Even when transferring to different reaction conditions, all of the samples must be exposed to identical reaction conditions. When the number of samples exceeds 1,000, it has not been possible to conduct reactions with different stages or expose individual samples to different reaction conditions. Additionally, in on-bead methods, in which separate samples are bound to beads, the beads have conventionally not been separated individually (spatially separated) for handling. This is because the development of a special device has been necessary for individual separation and handling. Even when such a device is employed, effort is required for separation and arrangement. Nor has any method (that is, method of rapidly transferring the samples in parallel fashion) facilitating the subsequent handling of the beads been proposed. No simple method of creating more than 1,000 different reaction conditions has been devised.

The simultaneous conducting of biochemical reactions such as PCR on substrates (plates) having multiple microwells is well known (Japanese Unexamined Patent Publication (KOKAI) Heisei No. 5-317030 (Patent Reference 1)). An improvement in which the capacity of the microwells is reduced and the reaction progresses favorably has also been made (WO2002/025289 (Patent Reference 2)). However, in conventional methods and devices employing multimicrowells in this manner, a reaction is simultaneously conducted with other samples, the conditions of each of the reactions are identical, and the reaction conditions of individual wells are not separately controlled.

DISCLOSURE OF THE INVENTION

There are numerous cases in which it is desirable to react identical samples in reaction solutions with different compositions to examine the results. However, such cases require that reaction solutions of differing composition be separately prepared for individual vessels (wells). However, when the number of microwells exceeds 1,000, such preparation becomes impractical, and such reactions are almost never conducted. Instead, a design of experiment is normally employed to conduct representative tests under various conditions, and results are deduced.

There are problems in that great effort is required to fill more than 1,000 vessels (wells) with reaction solution, and in that it is necessary to vary the composition during such filling.

Accordingly, the present invention has for its first object to provide a method for conveniently filling vessels (wells) with a solution such as a reaction solution, even when the vessels (wells) number in excess of 1,000, and even when the dimension, shape, and surface configuration of the vessels (wells) do not permit fluid to flow into the vessels (wells).

A second object of the present invention is to provide a method for simply filling vessels (wells) with a solution such as a reaction solution, even when the vessels (wells) number in excess of 1,000 and even when the dimensions, shape, and surface configuration of the vessels (wells) do not permit fluid to flow into the vessels (wells), by which the composition of the solution can be readily varied.

A particular object of the present is to provide a method permitting the above operation even when the capacity of the vessels (wells) is minute.

Means of Solving the Problem

The present invention solves the above-stated problems as follows:

[1] A method of introducing solution into the wells of a multiwell plate comprised of a substrate having multiple wells on at least one principal surface thereof, wherein
said wells are imparted dimensions, shapes, and surface configurations such that when said multiwell plate is positioned in stationary fashion with the openings of said wells facing upward, said solution does not enter said wells even when the openings of said wells are covered by said solution, and
said solution is positioned on said principal surface of said multiwell plate having wells and a centrifugal force oriented from the well opening toward the bottom is applied to introduce said solution into said wells.
[2] The method according to [1], wherein said centrifugal force is greater than or equal to 10×g.
[3] The method according to [1], wherein the maximum diameter of said well opening is less than or equal to 5 mm.
[4] The method according to [3], wherein said centrifugal force is greater than or equal to 20×g.
[5] The method according to [1], wherein the maximum diameter of said well opening is less than or equal to 1 mm.
[6] The method according to [5], wherein said centrifugal force is greater than or equal to 100×g.
[7] The method according to any one of [1] to [6], wherein said well capacity is less than or equal to 10 microliters.
[8] The method according to any one of [1] to [6], wherein said well capacity is less than or equal to 1 microliter.
[9] The method according to any one of [1] to [8], wherein said multiwell plate comprises 1,000 or more wells.
[10] The method according to any one of [1] to [9], wherein a filter having multiple openings is positioned on said principal surface, solution is placed on said filter, and a centrifugal force is applied from the well opening toward the bottom to introduce said solution into said wells through said openings of said filter.
[11] The method according to [10], wherein said solution is introduced into a portion of said multiple wells through said filter.

[12] A method of transferring at least a portion of the solution contained in at least a portion of the wells of a multiwell plate (2) comprised of a substrate having multiple wells on at least one principal surface thereof into the wells of a multiwell plate (1) comprised of a substrate having multiple wells on at least one principal surface thereof, wherein said wells of said multiwell plate (2) are imparted dimensions, shapes, and surface configurations such that when said multiwell plate (2) is positioned in stationary fashion with the openings of said wells facing downward, said solution does not flow out of said wells, and said multiwell plate (1) and said multiwell plate (2) are secured so that at least a portion of the wells of the two plates are aligned opposite each other and a centrifugal force oriented from the well openings of said multiwell plate (1) toward the bottoms thereof is applied to introduce the solution within the wells of said multiwell plate (2) into the wells of said multiwell plate (1).

[13] The method according to [12], wherein said wells of said multiwell plate (1) is imparted dimensions, shapes, and surface configurations such that when said multiwell plate (1) is positioned in stationary fashion with the openings of said wells facing upward, said solution does not enter said wells even when said openings of said wells are covered by said solution.

[14] The method according to [12] or [13], wherein a filter having multiple openings is positioned between said multiwell plate (1) and said multiwell plate (2) and a centrifugal force oriented from the well openings of said multiwell plate (1) toward the bottoms thereof is applied to transfer said solution through said filter openings.

[15] The method according to [14], wherein said solution is transferred through said filter into a portion of said multiple wells.

[16] The method according to any one of [12] to [15], wherein said wells of said multiwell plate (1) and said wells of said multiwell plate (2) are imparted identical hole dimensions, shapes, and arrangements.

[17] The method according to any one of [12] to [15], wherein at least a portion of said wells of said multiwell plate (1) and said multiwell plate (2) are imparted different hole dimensions, shapes, capacities, and arrangements.

[18] The method of any one of [12] to [17], wherein said centrifugal force is greater than or equal to 100×g.

Advantages of the Invention

The present invention permits the simultaneous, parallel handling (introduction, measuring-up, transferal, stacking, division, and measurement) of multiple extremely minute quantities of sample that has heretofore not been realized.

BEST MODE OF IMPLEMENTING THE INVENTION

Method of Introducing Solution

The first aspect of the present invention is a method of introducing solution into the wells of a multiwell plate comprised of a substrate having multiple wells on at least a principal surface thereof.

The multiwell plate (also sometimes referred to as a Multi Micro Vessel (MMV) (multiple parallel microvessel) hereinafter) employed in the method of the present invention is comprised of a substrate having multiple wells on at least a principal surface thereof. The multiple wells may be disposed on principal surfaces, or on a single principal surface thereof.

The number of wells disposed on a principal surface of the multiwell plate is not specifically limited; for example, the number may be 1,000 or more per square inch ($2.5 \times 2.5$ cm$^2$), within a range of from 1,000 to 100,000. The number of wells may be suitably determined based on the purpose for which the multiwell plate is being employed.

The capacity of the wells is not specifically limited, and may be suitably determined by taking into account the size of the substrate, the number of wells, the reaction (quantity of solution), and the like. For example, the capacity of the wells may be less than or equal to 10 microliters, or less than or equal to 1 microliter. The material of the substrate is not specifically limited; for example, the substrate may be comprised of plastic, silicon, or gel.

The wells have dimensions, shapes, and surface configurations such that when the multiwell plate is positioned in a stationary manner with the openings of the wells facing upward, the solution does not enter the wells even when the well openings are covered with the solution with which the wells are to be filled. That is, when the well openings are of a certain size and a certain quantity of solution is placed on the principal surface on which the wells are disposed, the solution naturally flows into the wells, filling them. However, when the dimensions of the openings of the cells are smaller than a certain size, surface tension prevents the solution from flowing naturally into the wells, requiring the use of a microsyringe to inject the solution. This phenomenon depends not only on the dimensions of the well opening, but also on the shape of the well opening and on the surface configuration of the well opening and surface conditions of the opening and interior of the well (particularly the surface conditions of the portion near the opening). Further, this phenomenon also depends on the physical properties of the solution (liquid) being introduced into the wells. The present invention is a method for introducing solution into the wells of a multiwell plate in which the solution will not flow naturally into the wells regardless of the quantity of solution that is placed on the principal surface in which the wells are provided.

For wells such that when a solution that is placed on a primary surface on which wells are provided will not naturally flow into the wells regardless of the quantity of solution provided, when the maximum diameter of the well openings is less than or equal to 5 mm, in most cases, the solution will not flow naturally into the wells, although this depends on the well dimensions, shape, and surface configuration. At less than or equal to 3 mm, the solution will normally not flow naturally into the wells. When the maximum diameter of the well openings is less than or equal to 1 mm, the solution will not flow naturally into the wells and an optimal effect is achieved by the method of the present invention.

The shape of the well opening is not specifically limited. By way of example, the opening may be round, angular (square or rectangular), diamond-shaped, or polygonal (for example, hexagonal or octagonal). The well opening may have a protruding lip or, conversely, a beveled edge.

The depth of the wells is suitably determined taking into account the dimension of the wells opening and quantity of the liquid with which the wells are being filled. Generally, the greater the ratio of the depth of the wells to the size of the well openings, the less likely it is that the solution will fill the wells. The method of the present invention is particularly effective when the ratio of the depth of the wells to the size of the well opening is greater than or equal to 1, and functions effectively even when the ratio of the depth of the wells to the size of the well opening is greater than or equal to 2. For example, the ratio of the depth of the wells to the size of the well opening falls within a range of 1 to 10, desirably 2 to 8, and preferably 2.5 to 5. However, the depth of the wells must always be suitably determined by taking into account the volume of liquid with which the wells are to be filled and the size of the well openings. The method of the present invention will function properly—that is, the wells can be filled with solution—even when the ratio of the depth of the wells to the size of the well opening exceeds 10. Based on the method of the present invention, a well without a bottom (such as a tubular well) may be employed. In that case, the conditions (for example, the centrifugal force) can be suitably adjusted to introduce solution to the center of the well (tube) and draw the solution out on the opposite side.

The thickness of the substrate constituting the multiwell plate is suitably determined taking into account the depth of the wells, the strength required of the multiwell plate, and the strength required of the bottoms of the wells. Normally, it is suitable for the thickness of the substrate to be about the same as, or greater than, the depth of the wells. It is possible for the four sides of the front surface and the surrounding edge of each well not to be worked at all, or for a raised lip of a certain height to be provided.

In the method of the present invention, solution is positioned on the principal surface of the above-described multiwell plate, on which the wells are located, after which a centrifugal force oriented from the well openings toward the bottom is applied to introduce the solution into the wells. The centrifugal force is suitably determined by taking into account the size of the well openings and the difficulty with which the solution tends to flow into the wells. For example, it may be 10×g or greater. By way of example, when the maximum diameter of the wells is less than or equal to 5 mm, the centrifugal force is desirably greater than or equal to 20×g. Further, when the maximum diameter of the well openings is less than or equal to 1 mm, the centrifugal force is desirably greater than or equal to 100×g, preferably falling into a range of 100 to 2,000×g. However, it is possible to apply an even greater centrifugal force, depending on the shape, volume, and the like of the wells.

The method of the present invention will be described with reference to FIG. 1. FIG. 1 is a descriptive drawing of an MMV installed in a centrifuging tube. Since the bottom of the centrifuging tube employed is not flat (but is spherical), the installation surface of the MMV within the centrifuging tube has been packed with agarose gel to render it horizontal (the surface of the agarose gel being horizontal). However, it is not necessary to employ agarose gel; some other material may be employed or a centrifuging tube with a flat bottom may be procured for use. The MMV is placed on the surface of the agarose gel within the centrifuging tube, and the sample solution that is to be packed into the wells of the MMV is introduced (on left in figure). In the figure, an *E. coli* solution is employed as the test solution. The centrifuging tube is then mounted in a centrifuge and centrifuged with a prescribed centrifugal force. The centrifugation causes the sample solution to enter the wells (on right in figure).

In the course of introducing the solution by centrifugation, it is possible for the installation surface of the MMV to be flat and for the sample solution to be filled to the top surface of the MMV; if filled to the top, it is possible to employ a jig in addition to the centrifuging tube. For example, it is possible to install the MMV in a container with a flat bottom, introduce the sample solution thereover, and manually rotate the container to apply a centrifugal force to introduce the solution into the wells of the MMV.

Based on the method of the present invention, a filter having multiple openings can be placed on the principal surface of a multiwell plate, a solution can be placed on the filter, and a centrifugal force oriented from the well openings toward the bottom can be applied, introducing the solution into the wells through the filter openings. The use of a filter makes it possible to introduce solution to just a portion of the wells. The pattern of filter openings can be suitably adjusted based on the application. FIG. 2 shows an example of a filter.

FIG. 2 shows filters 1 to 10. The black circles denote openings in the portion permitting solution to pass. A multiwell plate employing a combination of filters is shown in the lower right portion of the figure. The black circles denote wells arranged horizontally and vertically with 32 wells in each direction, totaling 1,024 wells.

In filter 1, a single row of openings (32 openings per row) is provided every other row, for a total of 16 rows.

In filter 2, two rows of openings (32 openings per row) are provided at intervals of two rows, for a total of 16 rows.

In filter 3, four rows of openings (32 openings per row) are provided at intervals of four rows, for a total of 16 rows.

In filter 4, eight rows of openings (32 openings per row) are provided at intervals of eight rows, for a total of 16 rows.

In filters 5 to 8, the horizontal and vertical configurations (rows and columns) of filters 1 to 4 have been reversed.

In filters 9 and 10, 16 rows or 16 columns of openings (32 openings per row or column) have been provided over half of the surface, for a total of 16 rows or 16 columns.

By using the above filters and varying the type of solution to introduce multiple solutions multiple times, it is possible to control the composition of the solutions in the wells. As shown in FIG. 2, 10 filters may be sequentially employed and a solution of different composition introduced into the MMVs with each filter. Specifically, filter 1 is mounted on the MMV and the centrifugation method of the present invention is used to simultaneously introduce solution. In this manner, solution is introduced into some wells and not into other wells based on the pattern of filter 1. This operation is then sequentially conducted for filters 2 through 10. In this manner, a selection is made ten times as to whether a given solution will be introduced into a given well or not. That is, this operation fills the wells with solutions in a manner affording $2^{10}$ possible combinations. That is, the 1,024 wells are filled with solutions having $2^{10}=1,024$ different compositions.

As shown on the lower right in FIG. 2, addresses 0 to 1023 are assigned to the wells from the well on the upper left of the MMV. These are then organized. When creating a solution environment of 1,024 types with 10 filters and denoting the solution status of each well with a 10 digit (the introduction of a solution with each filter is represented by a digit: the 10 filters are represented by 10 digits) base 2 number ("1" when a solution is introduced by a filter, "0" when it is not), the solution status of well 0 becomes [0000000000]. Well 1023 becomes [1111111111]. The use of filters in the method of the present invention in this manner permits the free and easy adjustment (with little effort) of the composition of the solution with which the wells are filled.

In the method of the present invention, the solutions with which the wells are filled are not specifically limited. Examples are the reaction solutions and culture solutions employed when reacting multiple minute liquid samples in evolutionary engineering, pharmaceuticals, food, bioventures, agencies of conducting clinical examinations, agencies of checking for the toxicity of compound substances, and the like. For example, multiple condition tests can be readily processed in parallel, such as the nutrient requirement tests (amino acids, sugars, vitamins, inorganic ions, and the like) conducted when identifying species of microbes and genetic mutation tests of certain biological species (that is, the investigation of new nutritional requirements and resistance to the environment). In particular, depending on the types of genes involved, there are cases where symptoms are light when any one single component is lacking but growth is inhibited when two or more components are simultaneously lacking. (This is seen in leaky mutants. This type of phenomenon is also seen when complementary metabolic systems are present.) At such times, the present invention is effective at probing which combinations of components are causative because it can simultaneously handle large numbers of combinations. The same applies to cases where two components are involved and quantity is an issue. For example, assuming interchangeability between Mg++ and Mn++ in certain types of enzymatic activity, when determining how to optimize their respective concentrations for example, by varying their concentrations over a range 0.1 mM to 1 M (assuming 30 conditions: 0.1 mM, 0.2 mM, 0.3 mM . . . ), the number of combinations alone becomes quite large (900 conditions). This can be conducted in just one run.

[Method of Transferring Solutions]

The second aspect of the present invention is a method for transferring at least a portion of the solution contained in at least a portion of the wells of a multiwell plate (2) comprised of a substrate having multiple wells on at least one principal surface thereof into the wells of a multiwell plate (1) comprised of a substrate having multiple wells on at least one principal surface thereof.

In the second aspect of the present invention, two multiwell plates are employed. The solution in the wells of one of the multiwell plates (2) is transferred to the wells of the other multiwell plate (1). The wells of multiwell plate (2) are imparted with dimensions, shapes, and surface configurations such that when multiwell plate (2) is stationary with the openings of the wells facing downward, the solution in the wells does not flow out of the wells. In all other regards, multiwell plate (2) is identical to the multiwell plate described in the first aspect above. Further, it is not necessarily required that multiwell plate (1) be imparted with dimensions, shapes, and surface configurations such that when multiwell plate (1) is stationary with the well openings facing downward, the solution in the wells not flow out of the wells; however, it is acceptable for such to be the case. Alternatively, in the same manner as in the multiwell plate described for the first aspect above, multiwell plate (1) may be imparted with dimensions, shapes, and surface configurations such that when the multiwell plate is stationary with the openings of the wells facing upward, solution does not enter the wells even when the openings of the wells are covered with solution. However, this is not a limitation. In all other regards, multiwell plate (1) may be identical to the multiwell plate described for the first aspect above.

In the second aspect of the present invention, multiwell plate (1) and multiwell plate (2) are secured so that at least a portion of the wells on the two plates are positioned opposite each other. A centrifugal force oriented from the openings of the wells of multiwell plate (1) toward the bottoms is applied, transferring the solution present in the wells of multiwell plate (2) into the wells of multiwell plate (1). This form is shown in FIG. 3. In the same manner as in form 1 above, the centrifugal force can be greater than or equal to 10×g, for example. Multiwell plates (1) and (2) are desirably secured so that the transfer of solution only takes place well between wells, with the principal surface of multiwell plate (1) on which the wells are located being in gapless, tight contact with the principal surface of multiwell plate (2) on which wells are located. Thus, the principal surfaces of the two plates desirably have good planar properties and smoothness. There are also cases when the use of a jig to secure the two plates is desirable.

The opening dimensions, shape, and disposition of the wells of multiwell plates (1) and (2) may be identical, as shown in FIG. 3, for example. Alternatively, the opening dimensions, shapes, capacities, and dispositions of at least some portion of the wells of multiwell plates (1) and (2) may differ. For example, the shape of the wells of multiwell plate (1) and the shape of the wells of multiwell plate (2) may be selected so that one opening on multiwell plate (1) corresponds to two or more openings on multiwell plate (2) (FIG. 4(A)). Alternatively, the shape of the wells of multiwell plate (1) and that of the wells of multiwell plate (2) may be selected so that two or more openings on multiwell plate (1) correspond to one opening on multiwell plate (2) (FIG. 4(B)). In such cases, the shapes of the openings of the individual wells can be selected so that the corresponding openings match up properly.

Further, as shown in FIG. (3), the wells of multiwell plates (1) and (2) can be secured so that all of the wells oppose each other, or secured so that a portion of the wells oppose each other (FIG. 4(C)). Further, the wells of multiwell plates (1) and (2) may have openings of identical shape, or may have openings of different shapes (FIG. 4(D)).

Additionally, a filter having multiple openings can be placed between multiwell plates (1) and (2) and a centrifugal force can be applied from the opening toward the bottom of multiwell plate (1) to transfer the solution through the filter holes. The filter employed here may be identical to that described in the first aspect above. The insertion of a filter permits the transfer of solution to some portion of the multiple wells. There is no limitation to the use of a single filter; multiple filters may be stacked for use. In this manner, with just a few filters, variation in the opening patterns can be increased.

EMBODIMENTS

The present invention will be set forth more in detail below.

Embodiment 1

Preparation of an MMV

Multiwell plates (MMV) come in dry types (SU-8 plastic and the like) and wet types (acrylamide gel). The use of an MMV prepared from acrylamide gel will be described in the present embodiment. However, the same implementation is possible with a multiwell plate of the dry type.

Powerful light from an ultra-high-pressure mercury lamp was passed through a fly-eye lens called an integrator so that blurred light struck the entire product uniformly. This was reflected and a pattern identical to the digital pattern data inputted by means of a computer was projected by a DMD™ onto a gel solution. Through the action of riboflavin while being struck with ultraviolet light, polymerization and gelling were induced. Conversely, when not struck by ultraviolet light, polymerization did not initiate, and the gel solution was eliminated as a liquid, forming spaces (FIG. 5). Using this principle, the two MMVs (a) and (b) of the forms shown in FIG. 6 were prepared.

A method of projection in stages was employed for IR irradiation in the MMV polymerization process to prepare MMVs with these two shapes (FIG. 7). MMV(a): UV light was first projected onto an entire gel solution to form a bedding gel to serve as the bottom of the wells. Gel solution was then applied over the bedding gel and UV radiation was projected to form wells. Subsequently, the gel was rinsed, removing ungelled solution from the wells. FIG. 8 gives the dimensions of the wells. (b): First, the gel solution was irradiated with UV radiation through a mask that formed small holes. Gel solution was then filled in over the gel, and irradiated with UV radiation using a mask that formed large holes. Subsequently, ungelled gel solution was removed by rinsing. The gel in which the double holes had been formed was then placed on a bedding gel that had been prepared in advance and adhered by irradiation with UV radiation.

The composition of the gel solution was as follows.

| | |
|---|---|
| 40% Bis-acrylamide (1:39) | 10 mL |
| 20× TBE buffer solution | 1.25 mL |
| Cane sugar | 12.5 mg |
| 0.001% riboflavin aqueous solution | mess-up (suitable quantity) |
| Total | 25 mL |

The bis-acrylamide (1:39) referred to here denotes a mixture of N,N'-methylenebisacrylamide and acrylamide in a weight ratio of 1:39. This solution was poured onto polymerized gel and irradiated with UV radiation using a mask pattern like a photoresist such as that shown in FIG. 7. Wells of uniform shape corresponding to the mask pattern were formed.

Embodiment 2

Culturing *E. coli* in an MMV

*E. coli* were cultured using an MMV as a reactor, which is one of the uses of an MMV.
[Method]
(1) The MMVs employed were 16 percent polyacrylamide gel MMVs having a total of 1,024 wells distributed 100 wells per 25 mm$^2$.
(2) Gel buffers of the MMVs and a sliced gel were substituted. Each MMV was gently vibrated for 45 minutes at 1×SSC 300 mL. This operation was conducted twice.
(3) The buffer in the wells of the MMVs, which had been substituted was removed. This was done by aspiration from the wells using paper that had been sterilized with dry heat.
(4) All of the wells in the MMV were filled with an *E. coli* solution that had been adjusted ahead of time to a concentration of green fluorescence protein-producing (GFP-producing) *E. coli* TOP010 such that each well in the MMV might contain one bacterium. The centrifugation method of the present invention (FIG. 1) was the method used to fill the individual wells of the MMV with *E. coli* solution. The *E. coli* solution did not flow into the individual wells of the MMV upon simple immersion in the *E. coli* solution; when a centrifugal force of about 1,000×g was applied, all of the wells were filled with *E. coli* solution.
(5) The MMV that had been filled with *E. coli* solution was transferred to a Petri dish, buffer-substituted sliced gel was placed on the MMV, the Petri dish was sealed with a 1×SSC atmosphere, and the bacteria were cultured for 18 hours at 37° C. in an incubator (FIG. 9).
(6) The fluorescence of the GFP following culturing was detected with a fluorescent intensity measuring device to detect growth of the *E. coli*. The results are given in FIG. 10.
[Replica Preparation]
An MMV was prepared with a pattern precisely identical to the original pattern of the MMV in which *E. coli* had been distributed based on probability and caused to proliferate.
[Method]
The MMV serving as the original for the preparation of the replica was the MMV in which *E. coli* had been cultured as set forth above.
(1) *E. coli* were cultured in an MMV in the manner described above for culturing *E. coli* in an MMV. The concentration of the *E. coli* solution was suitably adjusted so that, as shown in FIG. 10, when the wells were filled with *E. coli* solution centrifugation, there was a probability of both wells containing *E. coli* and wells not containing *E. coli* being present.
(2) A new MMV (buffer substituted at 1×SSC, solution in wells completely aspirated away) was stacked with the wells aligned on an MMV in which *E. coli* had been cultured. The assembly was placed in a centrifuging tube and centrifuged at 1,000×g to transfer the solution in the wells to new wells (FIG. 3).
(3) The wells of both MMVs were filled with LB solution and incubated for 18 hours at 37° C.
(4) Following culturing, GFP fluorescence was detected with a fluorescence intensity measuring device to determine growth of *E. coli*. The results are given in FIG. 11. The left side of the figure shows the original MMV, and the right side shows the MMV to which the transfer was made. The pattern of wells producing fluorescence that was detected is nearly identical, indicating that solution containing *E. coli* had been properly transferred between wells. In the above-described centrifugation, a portion of the *E. coli* solution remained in the wells of the original MMV, and when the solution was cultured, fluorescence was detected.

In the above-described embodiments, properly formed 1,024-well MMVs were employed. Centrifugal introduction was conducted in such a manner as to achieve a probability of one *E. coli* cell being present as the anticipated value in each cell. The cells were cultured at 37° C. As shown in FIG. 10, wells appeared permitting the measurement of successfully proliferating colonies. These wells had a Poisson distribution. This indicated that the *E. coli* cells had been simultaneously successfully introduced by centrifugation, and that the MMV had functioned as a vessel for culturing the *E. coli* cells. Since the fluorescence protein (green fluorescence protein, GFP) was enveloped by the *E. coli*, when viewed from the side, the fluorescence appeared as green light.

The MMV successfully employed in culturing and an identical 1,024-well MMV were stacked top-to-top and centrifuged to simultaneously transfer the samples (See FIG. 3). Fresh medium was introduced by centrifugation into the MMV that had been emptied by transferring the sample, culturing was conducted, and a replica with a (nearly) identical pattern was obtained (see FIG. 11). This indicated that simultaneous parallel transfer was possible.

FIG. 3 shows a single transferal of solution. FIG. 12 shows that successive transferal of multiple types of solution was possible. As a result, it was possible to fill the wells with a solution of desired composition. In this process, the above-described filters could be employed to suitably adjust the composition in the wells as desired.

INDUSTRIAL APPLICABILITY

The present invention is applicable to the area of the simultaneous and parallel separation of samples that is necessary when reacting multiple minute liquid samples in evolutionary engineering, pharmaceuticals, food, bioventures, agencies for conducting clinical examinations, agencies for checking for the toxicity of compound substances, and the like.

BRIEF DESCRIPTION OF THE DRAWINGS

FIG. 5 A drawing descriptive of the principle of preparing an MMV.

FIG. 6 A drawing descriptive of the method of preparing an MMV.

FIG. 10 The results of culturing with an MMV (an image based on a fluorescence intensity measuring device is shown above, and a photograph is shown below).

Figure 1:
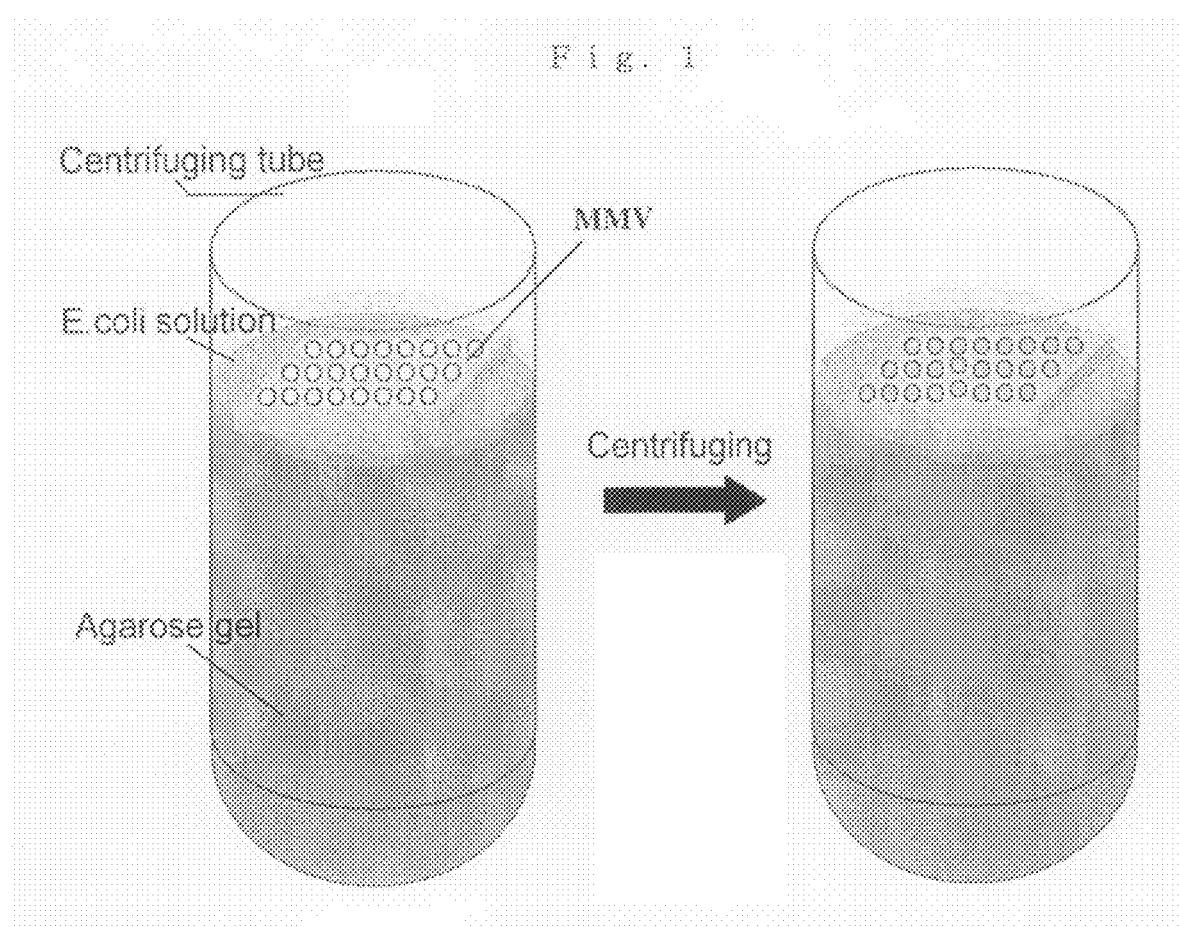
FIG. 1 A drawing descriptive of the method (first aspect) of the present invention.
Figure 2:
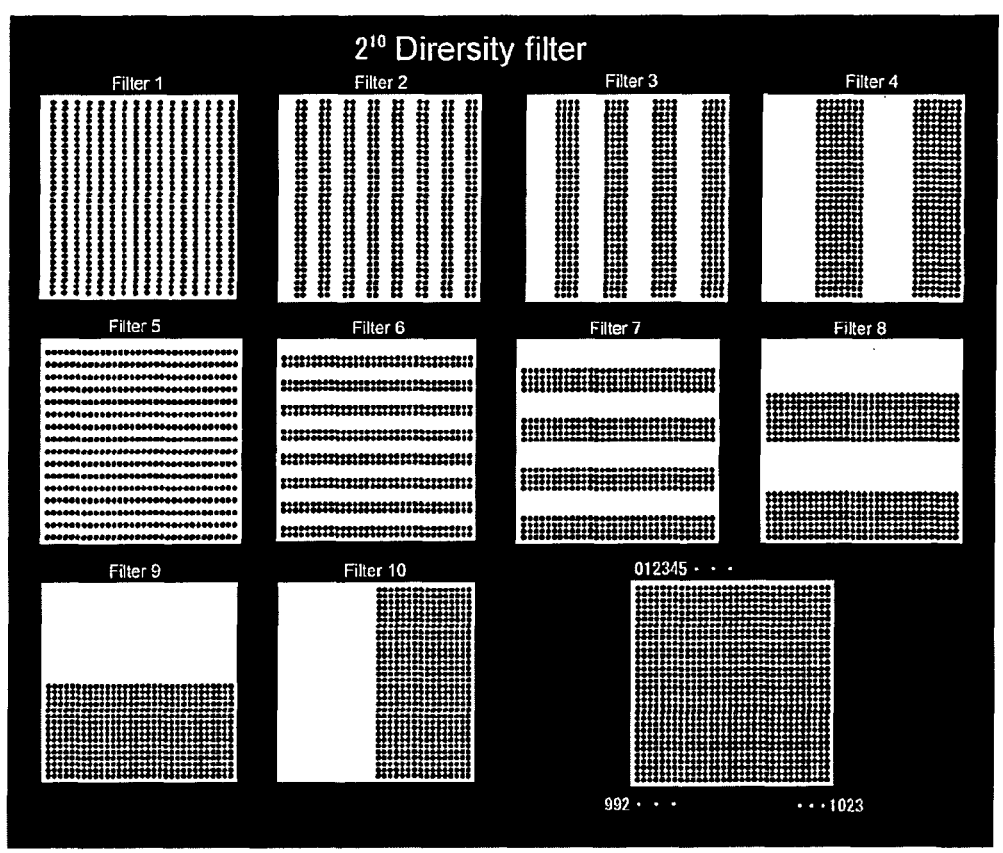
FIG. 2 A schematic diagram showing an example of a filter employed in the method of the present invention.
Figure 3:
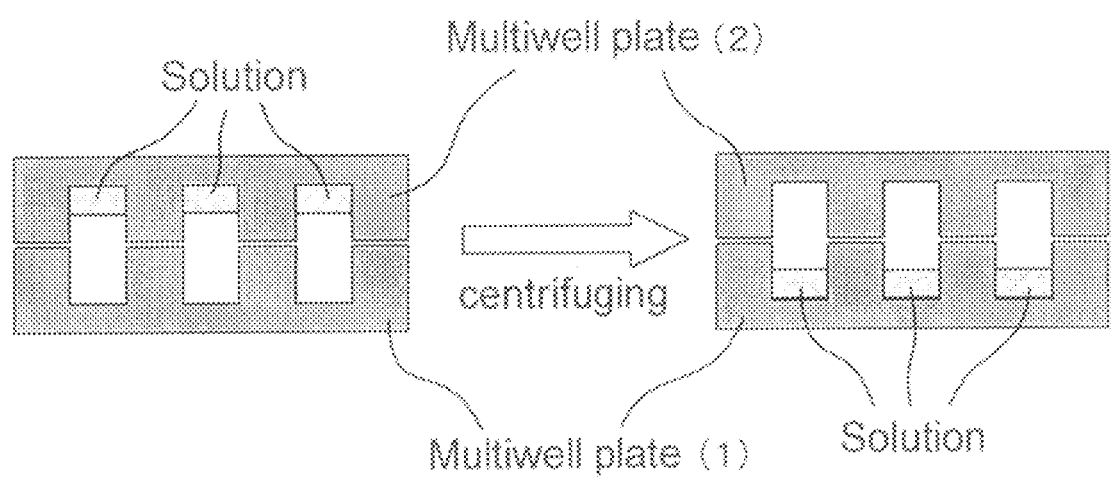
FIG. 3 A descriptive drawing of the method (second aspect) of the present invention.
Figure 4:
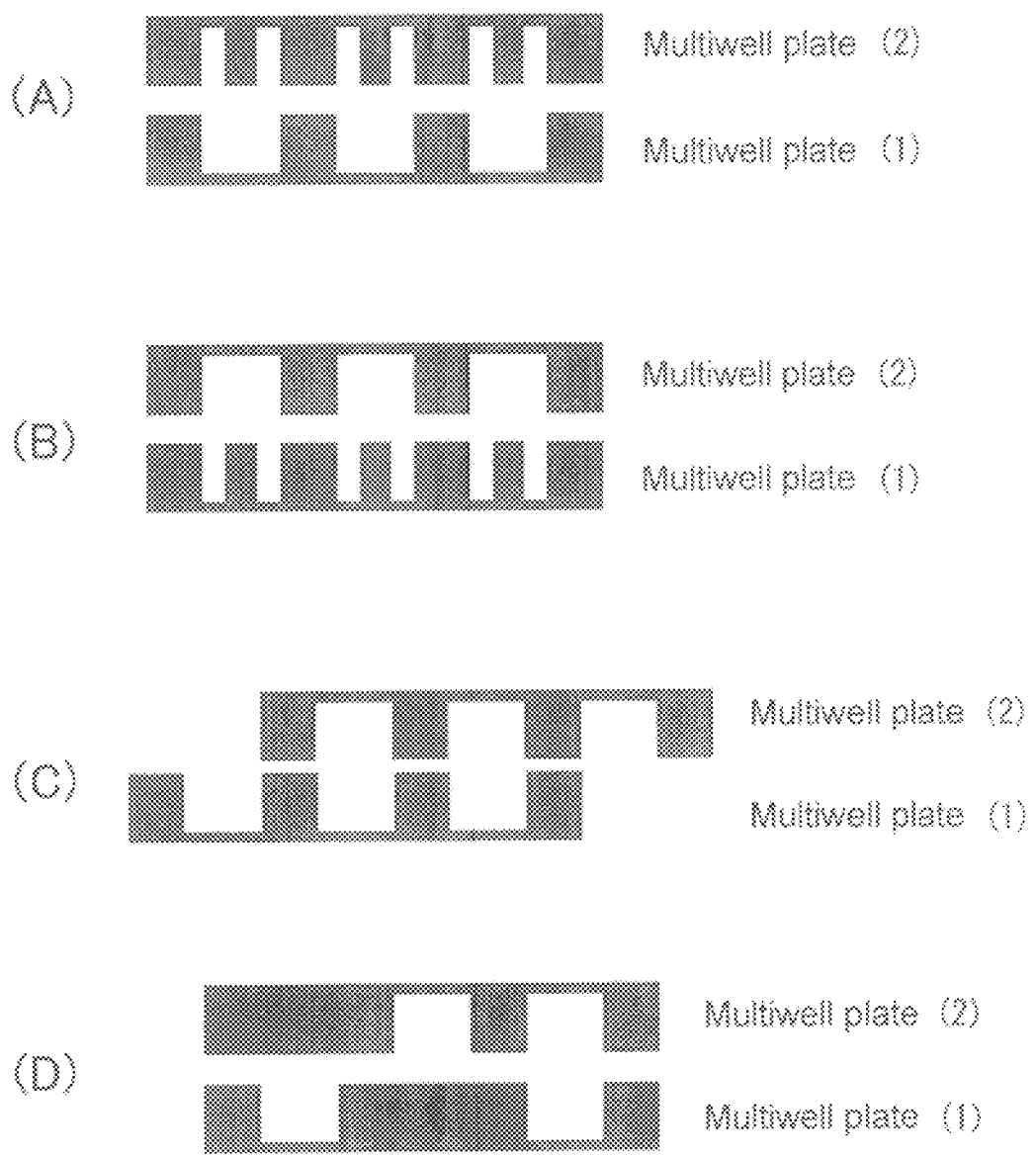
FIG. 4 A descriptive drawing of the method (second aspect) of the present invention.
Figure 7:
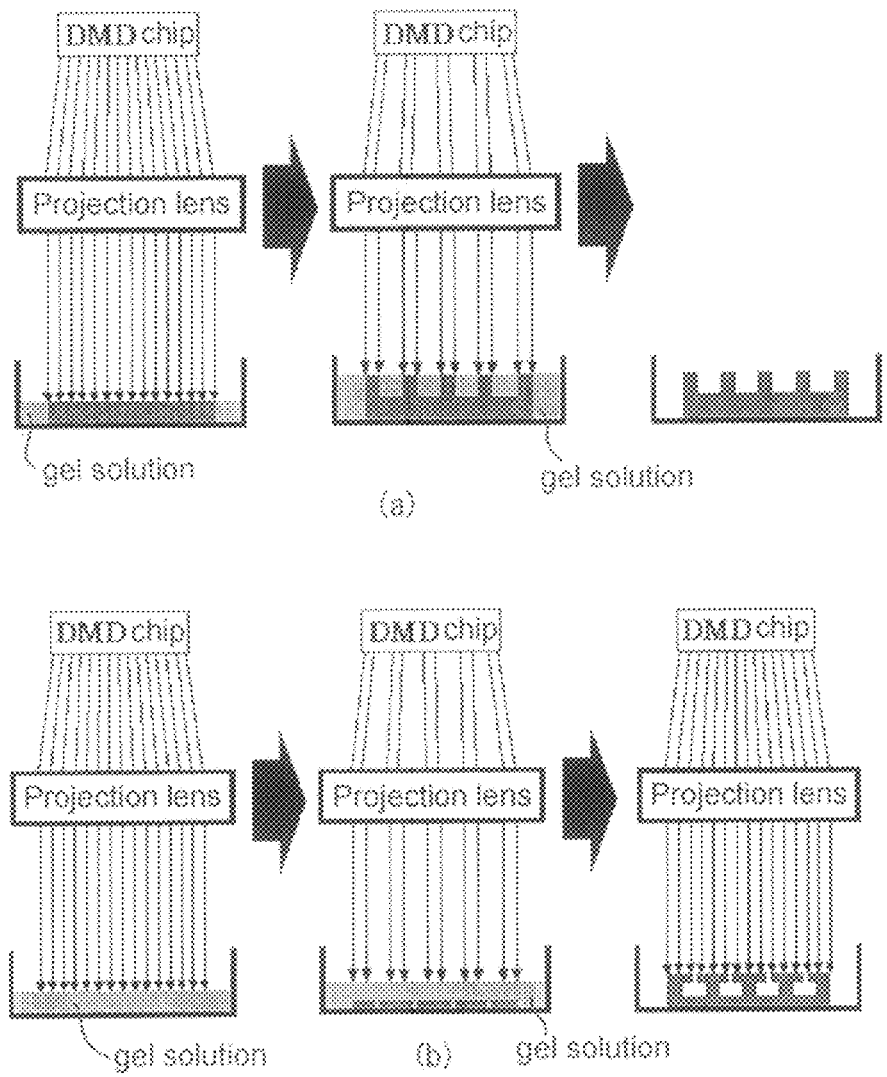
FIG. 7 A drawing descriptive of the method of preparing an MMV.
Figure 8:
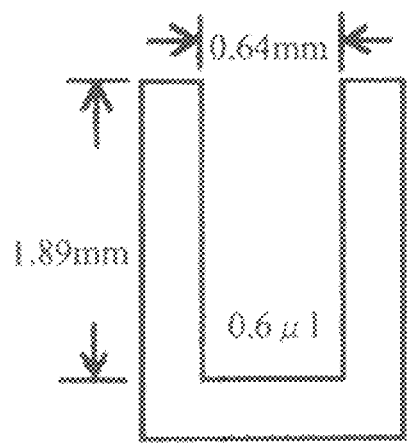
FIG. 8 A drawing descriptive of a single MMV well.
Figure 9:
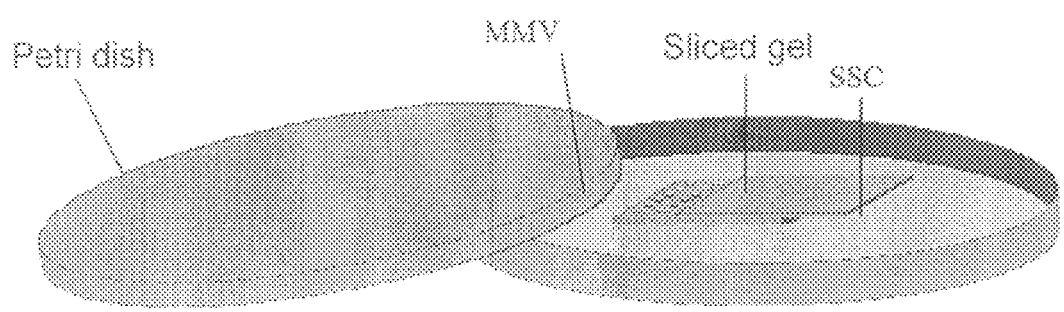
FIG. 9 A drawing descriptive of culturing using an MMV.
Figure 11:
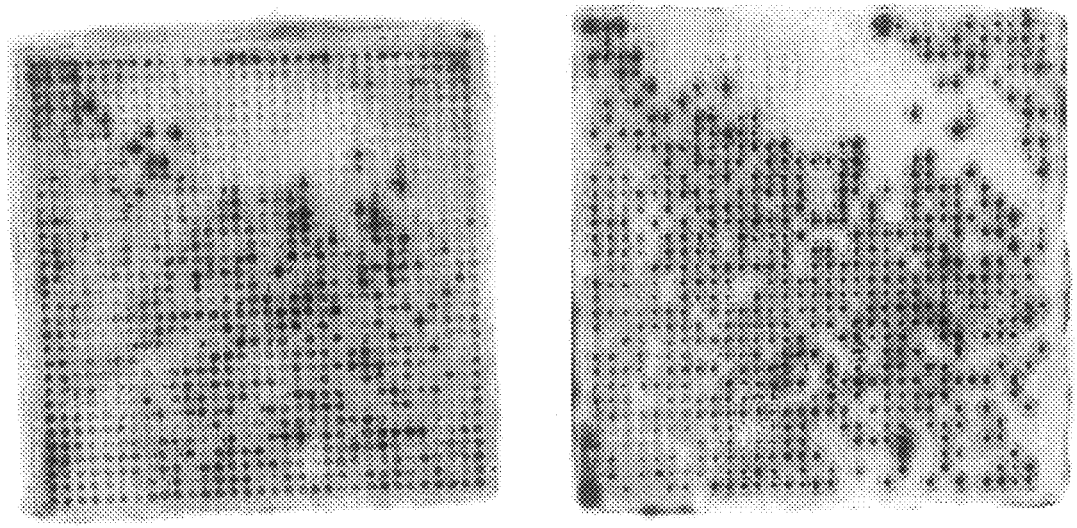
FIG. 11 An image based on a fluorescence intensity measuring device of how a replica is prepared (the original on the left, the copied replica on the right).
Figure 12:
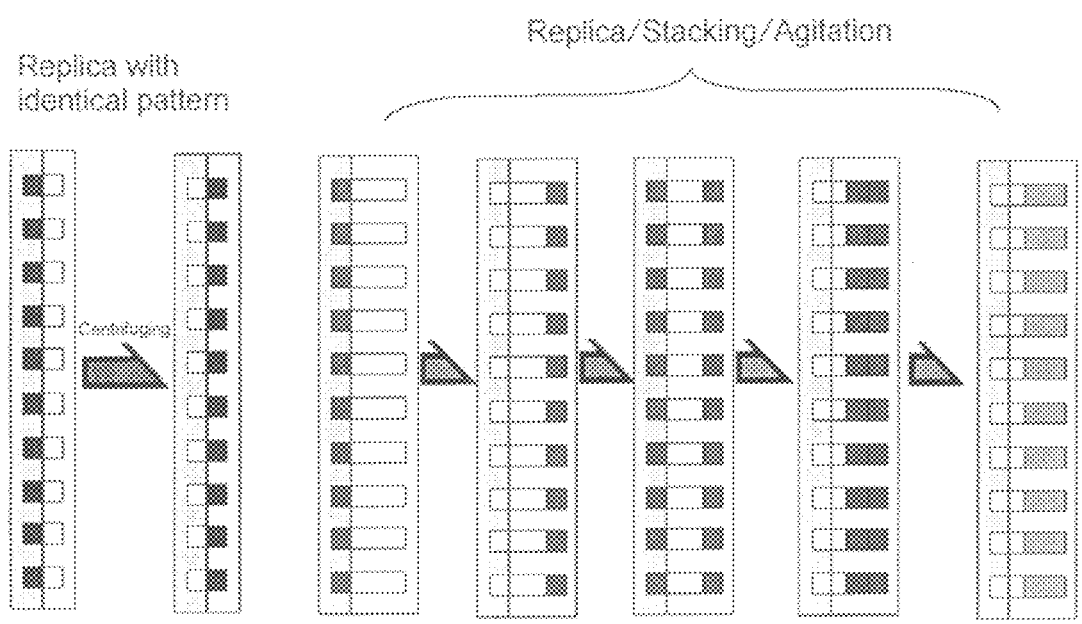
FIG. 12 A drawing descriptive of the sequential transferring of multiple solutions.

The invention claimed is:

1. A method of introducing solution into the wells of a multiwell plate comprised of a substrate having multiple wells on at least one principal surface thereof, comprising the steps of
    selecting a multiwell plate with wells having dimensions, shapes, and surface configurations do not allow said solution to enter said wells when said multiwell plate is positioned in stationery fashion with the openings of said wells facing upward, and the openings of said wells are covered by said solutions,
    positioning said solution on said principal surface of said multiwell plate, and
    applying a centrifugal force oriented from the well opening toward the well bottom to introduce said solution into said wells.

2. The method according to claim 1, wherein said centrifugal force is greater than or equal to 10×g.

3. The method according to claim 1, wherein the maximum diameter of said well opening is less than or equal to 5 mm.

4. The method according to claim 3, wherein said centrifugal force is greater than or equal to 20×g.

5. The method according to claim 1, wherein the maximum diameter of said well opening is less that or equal to 1 mm.

6. The method according to claim 5, wherein said centrifugal force is greater than or equal to 100×g.

7. The method according to claim 1, wherein said well capacity is less than or equal to 10 microliters.

8. The method according to claim 1, wherein said well capacity is less than or equal to 1 microliter.

9. The method according to claim 1, wherein said multiwell plate comprises 1,000 or more wells.

10. The method according to claim 1, wherein a filter having multiple openings is positioned on said principal surface, solution is placed on said filter, and a centrifugal force is applied from the well opening toward the bottom to introduce sail solution into said wells through said openings of said filter.

11. The method according to claim 10, wherein said solution is introduced into a portion of said multiple wells through said filter.

12. The method according to claim 1, wherein said solution is positioned on said principal surface of said multiwell plate having wells to cover at least part of the principal surface.

* * * * *